United States Patent [19]

Fogle

[11] 4,372,305
[45] Feb. 8, 1983

[54] METHOD OF TREATING DISEASED ORGAN

[76] Inventor: Harold W. Fogle, 2866 Crownview Dr., Rancho Palos Verdes, Calif. 90274

[21] Appl. No.: 222,251

[22] Filed: Jan. 2, 1981

[51] Int. Cl.³ .............................................. A61M 1/03
[52] U.S. Cl. ............................. 128/214 B; 128/214.2; 128/334 R
[58] Field of Search ................ 128/214 R, 214.2, 348, 128/334 C, 1 R, 214 B

[56] References Cited

U.S. PATENT DOCUMENTS

| | | | |
|---|---|---|---|
| 1,151,300 | 8/1915 | Soresi | 128/214 B |
| 1,585,628 | 5/1926 | Pfarre . | |
| 2,625,932 | 1/1953 | Salisbury | 128/214.2 |
| 2,625,933 | 1/1953 | Salisbury | 128/214 |
| 3,254,651 | 6/1966 | Collito | 128/334 C |
| 3,357,432 | 12/1967 | Sparks | 128/334 C |
| 3,483,867 | 12/1969 | Markovitz | 128/214 |
| 3,490,438 | 1/1970 | Lavender et al. | 128/214 R |
| 3,659,603 | 5/1972 | Oses | 128/214 B |
| 3,682,172 | 8/1972 | Freedman et al. | 128/214 |
| 3,699,960 | 10/1972 | Freedman | 128/214 |
| 3,788,319 | 1/1974 | Gillette | 128/214 |
| 4,047,526 | 9/1977 | Reynolds et al. | 128/214 |

OTHER PUBLICATIONS

Kimoto–Trans. Amer. Soc. Artific. Inter. Orgs., 1959, vol. 5, pp. 102–112.

*Primary Examiner*—Dalton L. Truluck
*Attorney, Agent, or Firm*—Fulwider, Patton, Rieber, Lee & Utecht

[57] ABSTRACT

There is disclosed a method for treating a diseased organ or organ system of an animal such as a human, by establishing the compatibility between a host and patient and then joining the arterial systems by making an incision over the femoral triangle to expose the common femoral artery from the inguinal ligament of both the patient and host. Such common femoral ateries are then transected and the open proximal end of the host or patient animal joined with the open distal end of the other animal by means of a graft and, vice versa, to thus provide arterial flow from the post to the patient to thus obtain a homogeneous mixture of blood throughout the arterial system of the patient without unduly traumatizing the blood.

15 Claims, 2 Drawing Figures

METHOD OF TREATING DISEASED ORGAN

BACKGROUND OF THE INVENTION

1. Field of the Invention:

The present invention relates to treatment of organs in a diseased patient.

2. Description of the Prior Art:

It has been common practice to withdraw blood from one patient for storage or treatment and to then enter that blood into the vascular system of a diseased patient or to merely circulate the blood of a diseased patient through a dialysis machine. However, to applicant's knowledge, a diseased patient has never been treated by joining his arterial system with the arterial system of a healthy person to attain full homogeneous blood flow through the diseased patient's arterial system.

SUMMARY OF THE INVENTION

The method of the present invention is characterized by direct joining of the arterial system of a host animal with the arterial system of a patient animal to provide for relatively unobstructed homogeneous blood flow through the arterial system of the patient. If necessary, the blood flow to or from the patient may be restricted to attain balanced flow between his arterial system and that of the host.

These and other features of the invention will become apparent from a consideration of the following detailed description of the drawings.

DESCRIPTION OF THE PREFERRED EMBODIMENT

The method of present invention may be utilized to join the arterial system of human beings or animals together for regression or resolution of a disease process or in experimenting therewith to better understand the etiology thereof. An example of a disease processes well understood is diabetes mellitus, wherein the patient is typically treated with controlled dosages of insulin naturally produced by the non-diabetic host, thus minimizing or even eliminating the necessity of treatment with exogenous insulin. Patients who may be treated with the present invention are those with diseases not so well understood such as those with advanced metastatic carcinoma, to seek regression or resolution of the disease from the affect of the physiologic mechanisms of the host.

It will be understood that the method of the present invention may be utilized in treating diseased animals such as human beings and that the reference herein to the patient and contemplate respectively, a diseased animal and reference to a host contemplates a healthy animal. In any event, the method contemplates that a host will be selected having a blood fully compatable with that of the patient depicted at 12 in FIG. 2 and, of course, in a method involving human beings, giving his consent to the procedure.

Figure 2:
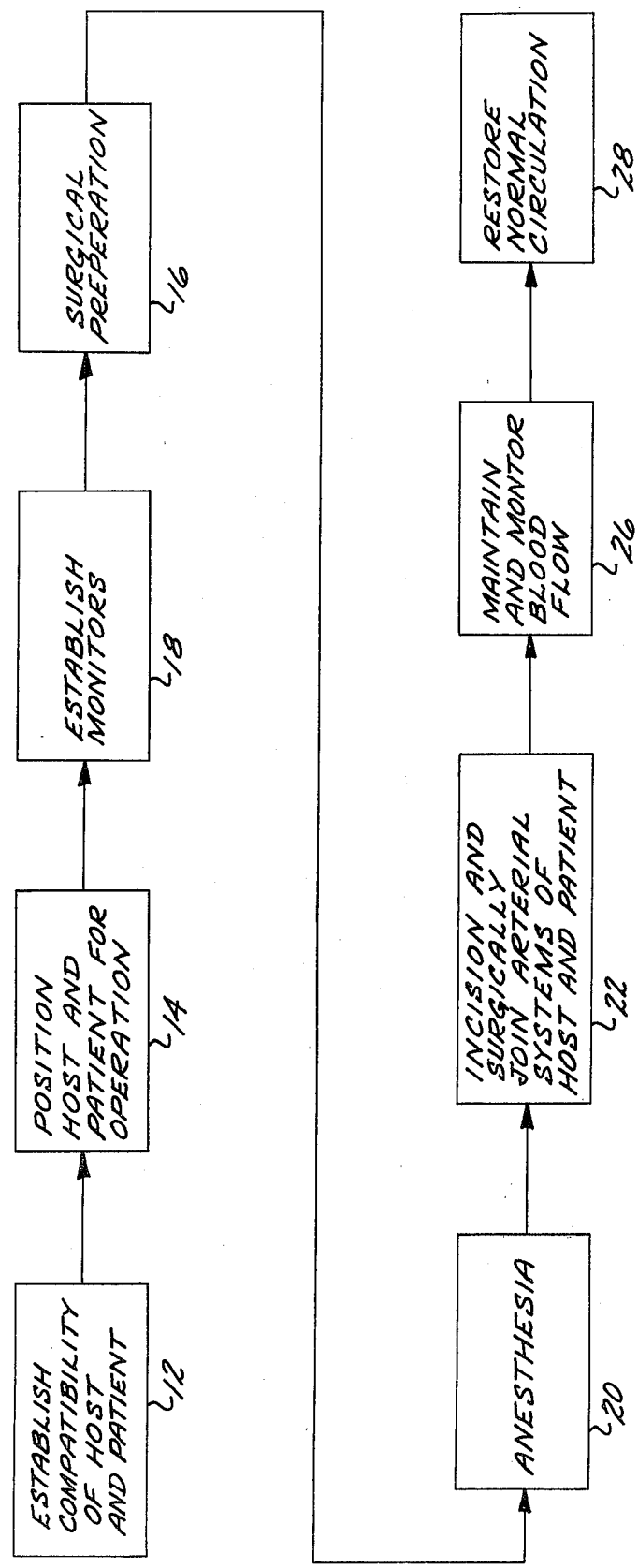
FIG. 2 is a diagramatic view of the method of the present invention.

The host and patient may then be positioned adjacent one another, as for instance, lying supine or reclining in a dual contoured chair as depicted at 14 in FIG. 2, and spaced only a few centimeters apart to minimize the length of graft necessary to join their arterial systems. The monitors are then established as depicted at 16, including arterial pressure (CVP), Swan-Ganz catheters, or any other parameters, the monitoring of which is desired, once the host has been selected. Blood chemistries, gas studies and all related base line studies desirable are conducted.

Figure 1:
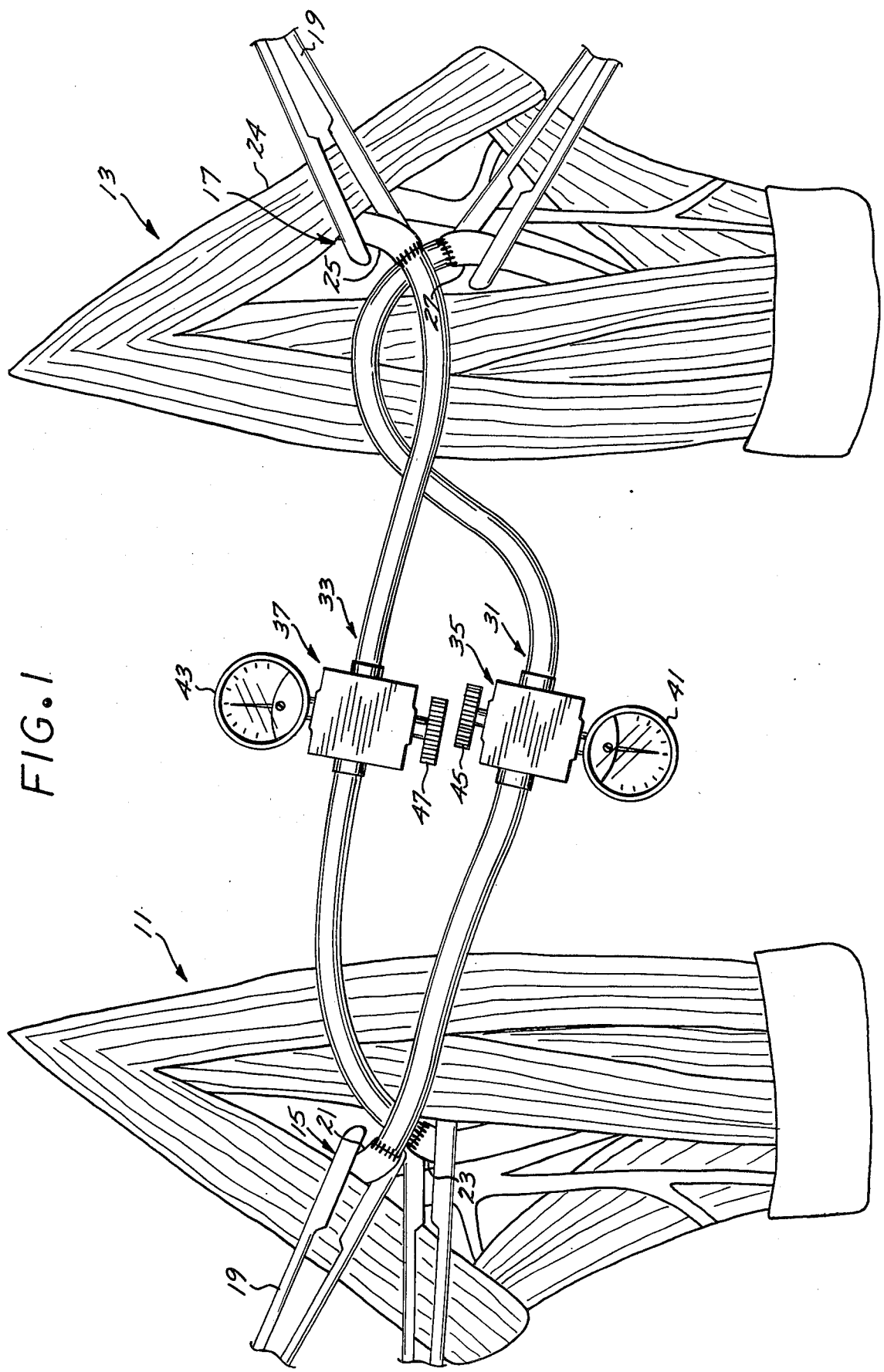
FIG. 1 is a top view showing the femoral triangles of a host and patient with the arterial systems thereof connected.

In the surgical preparation depicted at 18, the adjacent, femoral triangles 11 and 13 (FIG. 1), of the patient and host are prepared and draped.

Since the surgical technique is rather minor, the anesthesia may be local as depicted at 20 (FIG. 2). After full prepping, vertical incisions are made over the femoral triangles 11 and 13 of the host and patient as shown at 22 (FIG. 2), to expose the common femoral arteries from inguinal ligament 17, including bifurcation superficial and deep. Both patients are given 5,000 units of Heparin solution No. IV. Vascular clamps 19 are then applied to the common femoral arteries 15 and 17 at spaced apart locations to halt blood flow.

The common femoral arteries 15 and 17 of the host and patient are then transected at points between the clamps 15 and 17 to expose open proximal and distal ends 21 and 23, respectively, of the host artery 15 and the open proximal and distal ends 25 and 27 of the patient artery 17.

Anastamose gortex grafts about 8 mm. in diameter and of sufficient length to lead from the proximal end 21 of the host artery 15 to the distal end 27 of the patient artery 17 and, likewise, from the proximal end 25 of the patient's artery 17 to the distal end 23 of the host artery 15, are then selected.

If desirable, regulators, generally designated 35 and 37 may be installed in the respective grafts 31 and 33 for purposes which will appear hereinafter.

The graft 31 is sutured on one end to the proximal end 21 of the host's artery 15 and on its opposite end to the distal end 27 of the patient's artery 17 to thus form a shunt from the arterial system of the host to the patient. Likewise, one end of the graft 33 is sutured to the proximal end 25 of the patient's artery 17 and the opposite end thereof is sutured to the distal end 23 of the host's artery 15 to thus form a shunt from the patient's arterial system to the host's arterial system.

It will be appreciated that the regulators 35 and 37 are optional and may be of the character that include respective flow meters 41 and 43 to indicate the blood flow rate from the host to the patient and from the patient to the host, respectively. Such regulators 35 and 37 may include flow control valves operated by manual stems 45 and 47, respectively, such that the blood flow rate through the respective grafts may be adjusted independent of one another.

The vascular clamps 19 may be removed from the arteries 15 and 17 to thus establish blood flow from the host to the patient and from the patient to the host and the respective flows may be monitored as depicted at 26 (FIG. 2) by the respective flow meters 41 and 43. It is desirable to maintain such flows evenly balanced to thus arrive at a homogeneous blood mixture and avoid depriving either the host or the patient of blood volume. Such balance may be established by adjusting the valve stems 45 and 47 as dictated by the respective flow meters 41 and 43. It will be appreciated that in the event of any disturbance, the valves 45 and 47 may be closed rapidly to terminate blood flow.

It is preferrable to protect the respective shunts by sliding overlapping double transparent plastic sleeves to maintain the sterility thereof. The fascia and skin may be closed around the grafts 31 and 33 and such sleeve (not shown) sutured to the skin to maintain sterility.

The combined circulation may then be continued for the desired time period, all the while maintaining blood flow through the grafts 31 and 33 equal and monitoring the meters 41 and 43 to detect any clotting within the grafts, sepis, or any other indication of irregularities.

When the treatment period has been completed, the host and patient are re-prepped, drapped, anesthesized, the respective wounds opened and Heparin administered. The vascular clamps 19 are then applied simultaneously to the proximal ends 21 and 25 as well as the distal ends 23 and 27 of the respective arteries. The grafts 31 and 33 are then removed and end to end in anastomosis performed. The wound is then closed as depicted at 28, and both the host and patient tested for any irregularities and the base line studies compared.

From the foregoing, it will be apparent that the method of the present invention is relatively safe for the patient. Also, there is little likelihood of the host contracting cancer or other non-infectious diseases from the patient. Morbidity and mortality of this surgical procedure is low since the exposure and procedure is relatively simple and no vital organs are directly involved. Since the blood serves to mediate and communicate to the cellular level all the physiologic responses of the organism, all cells, both normal and abnormal, are exposed to all the physiologic responses of both host and patient.

I claim:

1. A method of treating a diseased organ or organ system of a patient, comprising the following steps:
    establishing the blood type of said diseased patient;
    selecting a healthy host having blood which is the same type as that of said patient and which matches with that of said patient;
    making surgical incisions to expose major arteries of said host and patient;
    surgically opening said arteries;
    selecting first and second tubes for accomodating substantially complete blood flow between said arteries;
    connecting said first tube between the proximal end of such host artery and the distal end of such patient artery;
    connecting said second tube between the distal end of such host artery and the proximal end of such patient artery;
    maintaining substantially equal rates of continuous blood flow from said proximal end of such host artery, through said first tube, to said distal end of such patient artery and from said proximal end of such patient artery to said distal end of such host artery to establish, for a selected period of time, flow of a homogeneous mixture of host blood with patient blood in the body of said patient to communicate said homogeneous mixture to said diseased organ or organ system;
    removing said tubes;
    closing said openings in said respective arteries;
    closing said incisions whereby said homogeneous flow of blood of the host and patient is communicated to the cells of said diseased organ or organ system for treatment thereof for said period of time.
2. The method of claim 1 wherein:
    said incision is made over a common femoral artery of said host and patient.
3. The method of claim 1 that includes the step of:
    placing a flow control meter in one of said grafts to control the rate of blood flow therethrough.
4. The method of claim 1 that includes the step of:
    controlling the rate of blood flow through at least one of said grafts.
5. The method of claim 1 that includes the step of:
    monitoring the rate of blood flow through both of said grafts;
    comparing said rate of blood flow; and,
    periodically adjusting the rate of blood flow through at least one of said grafts to maintain a substantially equal flow rate through both of said grafts.
6. The method of claim 1 wherein:
    said step of selecting said grafts includes selecting grafts of the type formed with flow passages which are substantially unobstricted.
7. The method of claim 1 wherein:
    said diseased organ is cancerous.
8. The method of claim 1 wherein:
    said patent is selected from the human race.
9. the method of claim 1 wherein:
    said patient and donor both selected from the human race.
10. The method of claim 1 that includes:
    the step of monitoring selected blood parameters of said patient during said selected period of time.
11. The method of claim 1 that includes:
    the step of injecting the incision areas with local anesthetic prior to making said incisions in said donor and patient.
12. The method of claim 1 that includes:
    the step of introducing anti-coagulant to the blood stream of said patient during said selected period of time.
13. The method of claim 1 that includes:
    the step of connecting said tubes with a regulator of the type which regulates blood flow;
14. The method of claim 1 that includes:
    the step of connecting said tubes with valves for controlling blood flow there through: and,
15. A method of treating an organ or organ system of a patient to have a diagnosed non-contagious disease and blood of a known type, including the following steps:
    selecting a donor of the type not having said diagnosed non-contagious disease and, further, of the type having blood of said known type and which is compatable with said known type of blood;
    surgically connecting one end of first tube means in the arterial system of said patient to receive blood from the patient's proximal arterial system and surgically connecting the opposite end of said first tube means in the arterial system of said donor to discharge blood to the donor's distal arterial system;
    surgically connecting one end of second tube means in the arterial system of said patient to receive blood from the patient's distal arterial system and surgically connecting the opposite end of said second tube means in the arterial system of said donor to discharge blood to the donor's proximal arterial system;
    maintaining said first and second tube means connected to said donor and patients' arterial systems for a selected period of time to maintain a continuous flow of a homogeneous mixture of said donor and patients' blood through the arterial system of said patient and donor.

* * * * *